United States Patent [19]
Roe

[11] Patent Number: 5,316,917
[45] Date of Patent: May 31, 1994

[54] AUTOMATED ANALYSIS OF FREE L-CARNITINE AND TOTAL SHORT-CHAIN ACYLCARNITINE

[75] Inventor: Diane S. Roe, Chapel Hill, N.C.
[73] Assignee: Duke University, Durham, N.C.
[21] Appl. No.: 971,888
[22] Filed: Nov. 4, 1992
[51] Int. Cl.$^5$ .............. C12Q 1/48; C12Q 1/54; C12N 9/02; A61K 43/00
[52] U.S. Cl. .................... 435/15; 435/14; 435/188; 435/117; 435/128; 435/190; 435/4; 435/7.91; 435/252.8; 560/145
[58] Field of Search ............ 435/15, 188, 190, 117, 435/128, 4, 7.91, 252.8; 424/1.1; 560/145

[56] References Cited

U.S. PATENT DOCUMENTS

4,221,869  9/1980  Vandecasteele et al. ........... 435/875
5,028,538  7/1991  Seim et al. ........................ 435/128

OTHER PUBLICATIONS

L. Bieber et al., *Federation Proceedings* 41, No. 12, 2858-2862 (1982).
G. Cederblad et al., *Clinical Chemistry* 32, No. 2, 342-346 (1986).
G. Cederblad and S. Lindstedt, *Clinica Chimica Acta* 37, 235-243 (1972).
C. Hoppel, in "Technique in Diagnostic Human Biochemical Genetics: A Laboratory Manual," (Wiley-Liss, Inc., 1991), pp. 309-326.
N. Kodo et al., *Clinica Chimica Acta* 186, 383-390 (1989).
N. Marquis and I. Fritz, *Journal of Lipid Research* 5, 184-187 (1964).
A. Marzo et al., *Journal of Chromatography* 527, 247-258 (1990).
J. McGarry and D. Foster, *Journal of Lipid Research* 17, 277-281 (1976).
S. Rodriguez-Segade et al., *Clinical Chemistry* 31, No. 5, 754-757 (1985).1
D. Seccombe et al., *Clinical Chemistry* 22, No. 10, 1589-1592 (1976).
Takeyama et al, *Analytical Biochemistry*, 158(2) pp. 346-354, (1986).
Xia et al, *Biochem & Biophy Res. Comm*, vol. 176(3), pp. 1617-1623, (1991).

*Primary Examiner*—Michael G. Wityshyn
*Assistant Examiner*—Louise N. Leary
*Attorney, Agent, or Firm*—Bell, Seltzer, Park & Gibson

[57] ABSTRACT

Disclosed is a method of assaying free L-carnitine and total short-chain acylcarnitine in blood. The method uses essentially protein-free samples of plasma or serum and comprises (a) obtaining a sample of ultrafiltrated plasma or serum, (b) converting essentially all carnitine to acetylcarnitine using an enzymatic reaction, (c) converting essentially all free coenzyme A liberated in the enzymatic reaction of (b) to thiophenylate, (d) evaluating the sample spectrophotometrically to determine the amount of thiophenylate present, (e) obtaining a fresh sample of ultrafiltrated plasma or serum and hydrolyzing the sample to convert essentially all short-chain acylcarnitine to carnitine, and (f) repeating steps (b) through (d). All steps following the ultrafiltration of the sample are carried out within a pre-programmed, automated centrifugal analyzer. The use of this method to measure only free L-carnitine or only total short-chain acylcarnitine in plasma or serum samples is also disclosed, as is a kit for carrying out the automated analysis of free L-carnitine and total short-chain acylcarnitine.

19 Claims, 1 Drawing Sheet

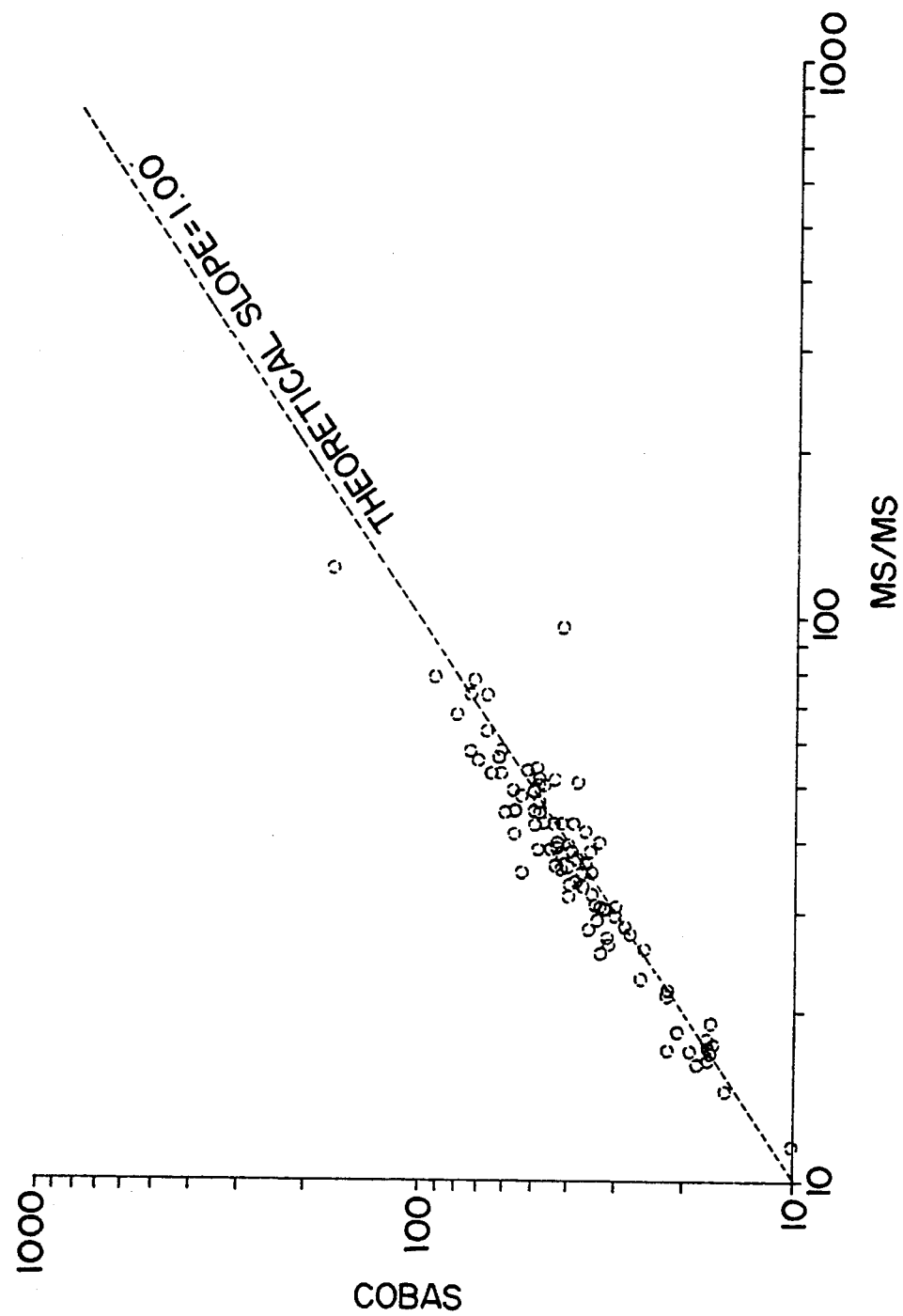

AUTOMATED ANALYSIS OF FREE L-CARNITINE AND TOTAL SHORT-CHAIN ACYLCARNITINE

FIELD OF THE INVENTION

The present invention relates to an automated spectrophotometric method for quantifying the free L-carnitine and total short chain acylcarnitine in an ultrafiltrated sample of plasma or serum.

BACKGROUND OF THE INVENTION

During the past ten years there has been an increasing awareness of the biochemical functions of L-carnitine, and of the clinical consequences of carnitine deficiency. See, e.g., Bieber et al., Fed. Proc. 41, 2858 (1982); Stanley, Adv. Pediatr. 34, 59 (1987). Carnitine is produced in the body in the form of L-carnitine. Both free L-carnitine and acylcarnitine are required for proper fatty acid oxidation within cells. A convenient, automated assay for free L-carnitine and total short chain acylcarnitine is needed for both research and clinical purposes. Certain inborn errors of metabolism result in the accumulation of toxic acetyl-coA; carnitine may be given to detoxify the acetyl-CoA. Patients receiving total parenteral nutrition and those on renal dialysis may have L-carnitine deficiencies. In each situation an assay for free L-carnitine and total short-chain acylcarnitine concentrations would be useful.

Several methods for assaying free L-carnitine and total short chain acylcarnitine are known in the art. See. e.g., Marzo et al., J. Chromatogr. 527, 247 (1990); Hoppel, In: Hommes (ed.), Techniques in Diagnostic Human Biochemical Genetics, New York, Wiley-Liss, 309–326 (1991). The most widely used methods are dependent on the enzyme carnitine acetyltransferase (CAT; EC 2.3.1.7), which catalyzes the reaction:

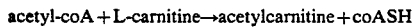

acetyl-coA + L-carnitine → acetylcarnitine + coASH where coASH represents free coenzyme A liberated.

One widely used spectrophotometric assay for carnitine is based on the reaction of the liberated coASH with 5,5'-dithiobis-2-nitrobenzoic acid (DTNB). This reaction produces the thiophenylate ion, which absorbs light at 412 nm. Spectrophotometric evaluation of a sample after reacting with DTNB provides an indirect measurement of free L-carnitine. See. e.g., Marquis and Fritz, J. Lipid Res. 5, 184 (1964). To assay acylcarnitine, alkaline hydrolysis of a sample can be used to convert acylcarnitine to free carnitine, and the steps above can then be used to measure total short-chain acylcarnitine.

Most methods currently in use are based on a partially automated version of these procedures, but require that several essential steps be performed manually by a technician. See, e.g., Seccombe et al., Clin. Chem. 22, 1589 (1976); Rodriguez-Segade et al., Clin. Chem. 31, 754 (1985); Cederblad et al., Clin. Chem. 32, 342 (1986). The manual steps required increase the potential for error and limit the convenience of these methods. Additionally the samples must be diluted, treated with thiol oxidizing reagent, or otherwise treated prior to analysis to remove biological interferences that affect the chemical reactions utilized in the assay.

The most widely used alternative to the spectrophotometric assay is a radioisotopic exchange assay (REA) that uses 1-$^{14}$C-acetyl-coA as substrate for the enzyme and measures the 1-$^{14}$C-acetylcarnitine produced. See Cederblad and Lindstedt, Clin. Chim. Acta. 37, 235 (1972). This method is generally accepted in the art as one of the most accurate, and several modifications have been described. See, e.g., Hoppel, In: Hommes (ed.), Techniques in Diagnostic Human Biochemical Genetics, New York: Wiley-Liss, 309 (1991); McGarry and Foster, J. Lipid Res. 22, 1589 (1976). However, this assay method is labor intensive and not suited to automation, and is therefore not routinely employed in clinical laboratories.

Mass spectrometry can also be used to measure total carnitine. While this method is currently used clinically, it is expensive and the number of hospitals equipped to perform it is limited.

In view of the foregoing, there is a continued need for new automated methods of assaying carnitine.

SUMMARY OF THE INVENTION

A first aspect of the present invention is an automated method of quantifying free L-carnitine in a plurality of biological fluid samples. The method comprises (a) adding a plurality of essentially protein-free biological fluid samples to a plurality of wells in a centrifugal spectrophotometric analyzer rotor; then (b) adding to each sample acetyl coenzyme A (coA) in an amount sufficient to react with essentially all the free L-carnitine in the sample to produce acetylcarnitine and free coenzyme A, and adding to each sample 5,5'-dithiobis-2-nitrobenzoic acid in an amount sufficient to convert to thiophenylate essentially all free coenzyme A produced by the reaction of free L-carnitine and acetyl coenzyme A (coA), and then (c) simultaneously adding to each sample carnitine acetyltransferase in an amount sufficient to convert essentially all free L-carnitine in the sample to acetylcarnitine and free coenzyme A; then (d) simultaneously spectrophotometrically determining the amount of thiophenylate present in each sample.

A second aspect of the present invention is an automated method of quantifying short-chain acylcarnitine in a plurality of biological fluid samples. The method comprises (a) adding a plurality of essentially protein-free biological fluid samples to a plurality of wells in a centrifugal spectrophotometric analyzer rotor; then (b) adding to each sample an alkaline solution capable of hydrolyzing essentially all acylcarnitine in the sample to free L-carnitine; then (c) adding to each sample acetyl coenzyme A (coA) in an amount sufficient to react with essentially all the free L-carnitine in the sample to produce acetylcarnitine and free coenzyme A, and adding to each sample 5,5'-dithiobis-2-nitrobenzoic acid in an amount sufficient to convert to thiophenylate essentially all free coenzyme A produced by the reaction of free L-carnitine and acetyl coA; then (d) neutralizing the pH of each sample; then (e) simultaneously adding to each sample carnitine acetyltransferase in an amount sufficient to convert of essentially all free L-carnitine in the sample to acetylcarnitine and free coenzyme A; then (f) simultaneously spectrophotometrically determining the amount of thiophenylate present in each sample.

A third aspect of the present invention is a kit for carrying out the automated analysis of free L-carnitine and short-chain acylcarnitine in blood. The kit comprises (a) a first container containing a solution comprising 5,5'-dithiobis-2-nitrobenzoic acid at a concentration of between 0.27 and 27 mmol/L and with a pH between 6.5–8.5; and (b) a second container containing a solution comprising acetyl-coenzyme A (coA) at a concentration between 1.2 mmol/L and 120 mmol/L, whereby the solutions of the first container and the second container can be mixed together prior to use to create a solution comprising 5,5'-dithiobis-2-nitrobenzoic acid at a concentration between 0.23 and 23 mmol/L and acetyl-coenzyme A at a concentration between 0.17 to 17 mmol/L.

BRIEF DESCRIPTION OF THE DRAWINGS

The present invention is explained in greater detail in the Examples, Detailed Description, and Figure herein, in which:

FIG. 1 is a graphed correlation of assays for free L-carnitine using the present method and isotope-dilution tandem mass spectrometry (MS/MS).

DETAILED DESCRIPTION OF THE INVENTION

The present invention is a spectrophotometric enzyme assay carried out using a programmable centrifugal analyzer and ultrafiltrated samples of serum or plasma. The previously known steps of reacting the sample with carnitine acetyltransferase and 5,5'-dithiobis-2-nitrobenzoic acid are utilized, as is alkaline hydrolysis of the sample. In the present invention ultrafiltrated samples of plasma or serum are used and the hydrolysis of acylcarnitine to free carnitine is a pre-programmed automated step carried out within the programmable centrifugal analyzer. Hydrolysis is monitored and calibrated by using standard solutions containing octanoylcarnitine.

Ultrafiltration is a simple and effective method for sample preparation that removes known interferences (such as thiol) and obviates the need to either dilute the samples or to treat them with thiol oxidizireagent prior to analysis. See. e.g., Wieland et al., In Bergmeyer (ed.) Methods of Enzymatic Analysis, 8th ed., 1985:481–488; Cejka and Kithier, Clin. Chem. 38, 304 (1992). The present method can utilize any filtration system capable of separating free microsolute ligands from that which is protein bound, and capable of producing essentially protein-free filtrate. By removing the proteins the thiols contained in the proteins are also removed. A preferred filtration system for use in the present method utilizes a membrane filter with a molecular weight cutoff of between 20,000 daltons and 40,000 daltons, and more preferably, with a cutoff weight of about 30,000 daltons. A preferred filter is an anisotropic hydrophilic membrane filter.

The present invention is designed to assay free L-carnitine and total short chain acylcarnitine using a programmable centrifugal analyzer, wherein the pipetting and mixing of reagents and solutions with samples are carried out automatically within the centrifugal analyzer, and wherein the spectrophotometric assessment of the samples is also performed as an automated step within the centrifugal analyzer. The spectrophotometric assessment preferably measures the absorption of light with a wavelength of between 400 and 420 nanometers.

To assay free carnitine in multiple samples of blood plasma or serum using the present method, multiple ultrafiltrated samples of blood plasma or serum are loaded into the sample rack of a programmable centrifugal spectrophotometric analyzer. The necessary solutions and reagents are also placed in specified rack positions. A cuvette rotor is installed and a pre-programmed assay initiated. The assay may be for free L-carnitine, total short-chain acylcarnitine, or both. In the assay for free L-carnitine, a specified amount of each sample is first transferred to an assay well on the rotor. A specified amount of solution containing 5,5'-dithio-bis-2-nitrobenzoic acid and acetyl coA is added to each rotor well containing a sample. The enzymatic start reagent containing carnitine acetyltransferase is placed in a side pocket in each assay well. In this manner the enzymatic start reagent is kept separate from the samples until centrifugation begins; all samples therefore undergo the same catalyzed reaction time. Centrifugation continues for a set time period and then each assay well is analyzed as it rotates past the spectrophotometric analyzer. In this way the multiple assay wells are evaluated essentially simultaneously.

The assay for total short-chain acylcarnitine utilizes a fresh sample of the ultrafiltrated blood plasma or serum, which is automatically transferred from the sample rack to an unused rotor well. The samples are hydrolysed to convert essentially all acylcarnitine to free L-carnitine. A specified amount of solution containing 5,5'-dithiobis-2-nitrobenzoic acid and acetyl coA is added to each rotor well containing a sample, and the pH of the samples is then neutralized. The enzymatic start reagent containing carnitine acetyltransferase is placed in a side pocket of each assay well and kept separate from the sample until centrifugation begins. Spectrophotometric evaluation is performed essentially simultaneously on the multiple samples.

Because the two assay procedures are preprogrammed and separable, it is a simple matter to assay only for free L-carnitine or only for short-chain acylcarnitine, or for both substances.

The present method is suitable for use in clinical laboratories. In the preferred mode described below, clinical analysis of more than 100 samples per working day can be completed by a single technician. The method has been validated by a recently developed isotope-dilution mass spectrometric reference method. See Kodo et al., Clin. Chim. Acta. 186, 383 (1989).

Another aspect of the present invention is, as noted above, a kit useful for carrying out the methods described herein. Such kits comprise separate containers containing some or all of the reagents and solutions necessary to assay free L-carnitine and short-chain acylcarnitine, with the containers typically contained within a single package. Preferably the kit contains a first container containing a solution of 5,5'-dithiobis-2-nitrobenzoic acid at a concentration of between 0.27 and 27 mmol/L and with a pH between 6.5–8.5, and a second container containing a solution of acetyl-coenzyme A (coA) at a concentration between 1.2 mmol/L and 120 mmol/L. The solutions of the first and second containers are mixed together prior to use, in proportions that produce a solution comprising 5,5'-dithiobis-2-nitrobenzoic acid at a concentration of between 0.23 and 23 mmol/L and acetyl coenzyme A (coA) at a concentration of between 0.17 and 17 mmol/L. Preferably the kit contains a third container containing carnitine acetyltransferase with a concentration of between 4 kU/L and 40 kU/L. More preferably, the third container contains an aqueous solution of carnitine acetyltransferase with a concentration of between 1.72 kU/L and 172 kU/L. Alternatively, the third container may contain lyophilized carnitine acetyltransferase capable of being diluted with water to produce a solution with a concentration of carnitine acetyltransferase between 1.72 kU/L and 172 kU/L. The kit may optionally contain a container holding an aqueous solution of L-carnitine at a concentration between 0.1 and 10 mmol/L, and an additional container holding a solution of 3-[N-morpholino]propanesulfonic acid in hydrochloric acid at a concentration of between 0.01 and 10 mol/L. The package may also optionally include instructions, typically on a printed sheet contained within the package or printed on the package itself, detailing the use of the elements of the kit for carrying out the methods described herein, with the instructions optionally including the proper programming instructions for programmable centrifugal analyzers for carrying out the methods as described herein. Of course, the instructions may be included with the kit by other means, such as by including a computer readable form (e.g., a floppy diskette) in the kit.

The present invention is explained in greater detail in the following non-limiting Examples.

EXAMPLE 1

Apparatus and Assay Procedure

This example describes a preferred apparatus for practicing the present invention and the preferred procedure for carrying out free L-carnitine and total short-chain carnitine assays.

A Cobas Fara II centrifugal analyzer (Roche Diagnostics, Montclair, N.J.) was used. Ultrafiltration was carried out using Centrifree TM filters with YMT membranes (Amicon Corp., Beverly, Mass.).

The reagents and solutions required for the assay are listed below. Some of the following solutions are similar to those described previously. See, e.g., Wieland, et al., In: Bergmeyer (ed.) Methods of Enzymatic Analysis, 8th ed. 1985:481–488. The solutions were stored at 0°–4° C. Distilled, de-ionized water from an in-house still was used to prepare and dilute the solutions. Abbreviations used: CAT, carnitine acetyltransferase; DTNB, 5,5'-dithio-bis-2-nitrobenzoic acid; EDTA, ethylenediaminotetraacetate; HEPES, 4-(2-hydroxyethyl)-1-piperazineethanesulfonic acid; MOPS, 3-[N-morpholino]propanesulfonic acid.

Solution 1: DTNB (2.7 mmol/L); HEPES 0.5 mol/L); EDTA (10 mmol/L) adjusted to pH 7.5 using NaOH (1 mol/L).

Solution 2: Acetyl-coA 12 mmol/L, prepared daily).

Solution 3: MOPS-HCl (1M) (20.93 g MOPS in 80 mL 1 mol/L HCl, made up to 100 mL with distilled water).

Solution 4: KOH (1 mol/L).

Primary reagent mixture (prepared daily): Solution 1 (1.8 mL) was mixed with solution 2 (0.3 mL) to provide final concentrations (mmol/L) as follows: DTNB 2.3; HEPES 428; EDTA 8.6; acetyl-coA 1.7. This amount was sufficient for one cuvette rotor (23 samples plus 5 calibration standards).

Enzymatic start reagent (prepared daily): CAT from pigeon breast muscle; (100 μL, 2.0 g protein/L; 96 U/mg protein) was diluted with water (900 μL) to a final concentration of 17.2 kU/L.

Stock solution and standard solutions: The stock solution contained 1 mmol/L each of L-carnitine and octanoyl-L-carnitine, prepared by dissolving L-carnitine hydrochloride (4.93 mg) and octanoyl-DL-carnitine hydrochloride (16.16 mg) in distilled water (25 mL). Solutions containing 100, 40, 30, 20 and 10 μmol/L each of L-carnitine and octanoyl-L-carnitine were prepared by dilution of the stock solution.

Enzyme concentration is important for reproducibility of the assay. Concentrations vary between different lots and suppliers, hence care must be taken to accurately dilute the enzyme solution to the specified final concentration.

Samples for analysis on the Cobas Fara II were prepared as follows. Serum or plasma (350 μL minimum per assay, collected with heparin or EDTA) was eluted through an Amicon Centrifree TM filter by centrifugation in a 45° fixed-angle rotor at 1000–2000 x g for 30 minutes. The Amicon Centrifree TM filter is an anisotropic hydrophilic ultrafiltration membrane with a molecular weight cutoff of 30,000 daltons. At least 150 μL of the ultrafiltrate was placed in a sample cup for assay. The aqueous standards for calibration were prepared in the same manner to compensate for any loss of acylcarnitine on the filter.

Test parameters were programmed for the Cobas Fara II centrifugal analyzer as indicated in Table 1. For free L-carnitine, reagent programming was set up for a "two reagent chemistry" with the primary reagent mixture in position 1 and the enzymatic start reagent (CAT) in position 2. For total short-chain acylcarnitine, programming was for a "three reagent chemistry" with the primary reagent mixture in position 1, solution 3 (MOPS-HCl) in position 2 and the enzymatic start reagent (CAT) in position 3. Solution 4 (1M KOH) was programmed as an alternate "diluent solution" to be pipetted in parallel with sample and placed in an assigned position on the same reagent rack. The standard solutions were loaded into the calibration rack and patient samples into an assigned sample rack. The primary reagent and enzyme solutions were placed with solutions 3 and 4 in assigned positions on the reagent rack. When programmed as a "profile", free L-carnitine was assayed first, followed by total short-chain acylcarnitine. The procedure took about 90 minutes for a full rotor of 29 cuvettes, allowing for set-up. For free L-carnitine determination only, a full rotor was analyzed in only 15 minutes. Results were identical using either end-point or kinetic calculations. The kinetic method was employed in all examples presented herein.

TABLE 1

| FREE L-CARNITINE | TOTAL SHORT-CHAIN ACYL CARNITINE |
|---|---|
| GENERAL | GENERAL |
| Measurement Mode: ABS | Measurement Mode: ABS |
| Rxn Mode: P-I-SR1-A | Rxn Mode: S-I-W-SR1-I-R1-I-SR2-A |
| Calibration Mode: Lin Reg | Calibration Mode: Lin Reg |
| Reagent Blank: Reag/Dil | Reagent Blank: Reag/Dil |
| Wavelength: 412 | Wavelength: 412 |
| Temperature: 37° C. | Temperature: 37° C. |
| Unit: μmol/L | Unit: μmol/L |
| ANALYSIS | ANALYSIS |
| P Sample Vol: 25 μL | S Sample Volume: 40 μL |
| Diluent Name: H$_2$O | Diluent Name: KOH |
| Vol: 5 μL | Vol: 5 μL |

TABLE 1-continued

| FREE L-CARNITINE | TOTAL SHORT-CHAIN ACYL CARNITINE |
|---|---|
| Cleaner Cycle: off | Cleaner Cycle: off |
| Reagent Volume 30 μL | |
| I Incubation: 150 s | I Incubation: 480 s |
| M1: 20 s | M: No |
| M2: 140 s | M: No |
| SR1 Start Reagl: 10 μL | W Wait Time: 480 s |
| Diluent Name: H₂O | SR1 Start Reagl: 5 μL |
| Vol: 5 μL | Diluent Name: H₂O |
| Wet Cycle: on | Vol: 0 μL |
| A Readings: | Wet Cycle: off |
| First: 1.0 s | I Incubation: 240 s |
| Number: 27 | M: No |
| Interval: 20 s | M: No |
| M: No | R1 Reag 1: 30 μL |
| M: No | I Incubation: 150 s |
| | M1: 20 |
| CALCULATION | M2: 140 s |
| Reaction Direction Increase | SR2 Start Reag 2: 10 μL |
| Check: On | Diluent Name: H₂O |
| Calculation Step A: Kinetic | Vol: 5 μL |
| First: 1 | Wet Cycle: On |
| Last: 27 | A Readings: |
| | First: 1.0 s |
| CALIBRATION | Number: 27 |
| Cal. Interval: Each Run | Interval: 20 s |
| Number of Stds: 5 | M: No |
| Position of Stdl: 1 | M: No |
| STD1: 10.0 STD2: 20.0 | |
| STD3: 30.0 STD4: 40.0 | CALCULATION |
| STD5: 100.0 | Reaction Direction: Increase |
| | Check: On |
| | Calculation Step A: Kinetic |
| | First: 1 |
| | Last: 27 |
| | CALIBRATION |
| | Cal. Interval: Each Run |
| | Number of Stds: 5 |
| | Position of Stdl: 1 |
| | STD1: 20.0 STD2: 40.0 |
| | STD3: 60.0 STD4: 80.0 |
| | STD5: 200.0 |

EXAMPLE 2

Assay of Total Short Chain Acylcarnitine

This example demonstrates the effectiveness of the apparatus and assay procedure described in Example 1, above, in assaying total short-chain acylcarnitine.

The effectiveness of the programmed hydrolysis for total short chain acylcarnitine determination was assessed by using the stock solutions (free L-carnitine and octanoyl-L-carnitine in equimolar amounts diluted to create five solutions containing 100, 40, 30, 20, and 10 μmol/L of L-carnitine and octanoyl-L-carnitine). Thus, two standard curves were obtained from the five standard solutions, one for free L-carnitine and the other for total short-chain acylcarnitine.

The values obtained by the present method were consistently within ±5% of the expected values of 10, 20, 30, 40 and 100 μmol/L for free carnitine and 20, 40, 60, 80, and 200 μmol/L for total carnitine. The errors were randomly distributed about the mean. Linear regression analysis of the data from 10 consecutive calibrations for free and total carnitine indicated a slope of 1.00 ($r^2$=0.999). (Data not shown). Samples of plasma ultrafiltrates hydrolyzed outside the centrifugal analyzer in a non-automated step and then assayed for free L-carnitine gave the same results as duplicate samples assayed using the present method's programmed conditions. A solution of the pure octanoylcarnitine standard used in the assay (100 μmol/L) contained no detectable free L-carnitine using the present method.

EXAMPLE 3

Validation of Assay Procedures by Mass Spectrometry

This example demonstrates the use of mass spectrometry to validate the assay procedures described in Examples 1 and 2, above. A VG QUATTRO tandem quadrupole mass spectrometer fitted with a cesium atom gun for secondary ion mass spectrometry (Fisons-VG Instruments, Danvers, Mass.) was used.

For tandem mass spectrometry (MS/MS) analysis, sample preparation was performed by a modification of the method described previously. See Kodo et al., Clin. Chim. Acta 186, 383 (1989). To plasma or serum (100 μL) the following internal standards were added: [$^2$H₃-methyl]-L-carnitine (4 nmol); acetyl-[$^2$H₃-methyl]-L-carnitine (0.5 nmol); $^2$H₅-propionyl-L-carnitine (0.1 nmol); isovaleryl-[$^2$H₃-methyl]₃-DL-carnitine (0.1 nmol) and octanoyl-[$^2$H₃-methyl]-L-carnitine (0.1 nmol). Ethyl alcohol (800 μL) was added and the mixture vortexed and centrifuged (13,000 x g, 5 minutes). The supernatant was washed with hexane (1 mL), evaporated under nitrogen and the residue incubated with 140 g/L boron trifluoride in n-butanol (100 μL, 65° C., 15 minutes). The solution was again evaporated and reconstituted in 50 μL of methanol:glycerol (1:1) containing sodium octyl sulfate (10 g/L).

About 2 μL of sample were placed on the sample probe for analysis by tandem mass spectrometry. Ions were produced by bombarding the sample with cesium ions at 10 keV. Selective detection of L-carnitine and its internal standard was accomplished by means of the "precursors of m/z 103" scan function previously reported. See Kodo et al., Clin. Chim. Acta 186, 383 (1989). The acylcarnitines were analyzed in the same sample by switching to a "precursors of m/z 85" scan function. To quantify free L-carnitine, the ratio of signals at m/z 218 and 221, corresponding to carnitine and [$^2$H$_3$-methyl]-carnitine was measured directly and compared with a standard curve. Similarly, the amounts of acetyl, propionyl, isovaleryl (C-5) and octanoyl (C-8) carnitines were quantified using their respective internal standards and ion ratios. To quantify C-4 and C-6 acylcarnitines, the internal standard for isovalerylcarnitine was employed. The sum of the individual short-chain acylcarnitine determinations was compared with the short-chain acylcarnitine value from the present invention.

Free L-carnitine and total short-chain acylcarnitine determinations for 92 random plasma samples were performed using both the present invention and mass spectrometry methods. The differences between individual measurements ranged from 1% to 30%, the mean difference being 10.5%. The results for free L-carnitine, which ranged in value from 10 to 168 μM, are plotted in FIG. 1. Linear regression analysis of these data indicated a slope of 1.17 ($r^2=0.90$; $y=1.17x-3.5$). For the total short-chain acylcarnitine data, the slope was 1.08 ($r^2=0.93$; $y=1.08 x-1.7$). (Data not shown.) Thus the values for carnitine given by the present method are typically about 10% higher than those given by the reference method. In previous comparative studies, spectrophotometric assays have given values higher than those determined by radioenzymatic assay by about the same order of magnitude. See, e.g., Cederblad et al., Clin. Chem. 32, 342 (1986); Cejka and Kithier, Clin. Chem. 38, 304 (1992).

These data support a conclusion that there is no chemical interference occurring in the present assay method.

EXAMPLE 4

Analytical Parameters

This example demonstrates the analytical parameters of the present invention as embodied in the mode described in Example 1.

Recovery of Added Carnitine: The recovery by the present method of L-carnitine (50 μmol/L and 200 μmol/L) added to plasma ultrafiltrates was 96±3% (mean±SD); the recovery of added octanoylcarnitine, determined as free carnitine after hydrolysis, was 101 ±3%. The recoveries for these standards added to plasma prior to filtration were 97±3% and 77±3% respectively, indicating the partial binding of octanoylcarnitine to plasma proteins, which are retained by the filter. The calculated recovery of decanoylcarnitine from plasma was about 53%. Longer chain length species were not recovered from the filter, owing to their binding to plasma proteins as reported previously. See Hoppel. In: Hommes (ed.) Techniques in Diagnostic Human Biochemical Genetics, New York: Wiley-Liss, 1991:309-326. Thus in ultrafiltrated samples, the analytical recovery for free L-carnitine and acylcarnitines up to C-8 was essentially 100%.

Specificity. The present method was used to compare free carnitine determination in untreated plasma and plasma ultrafiltrates, both with and without preliminary thiol oxidation. The results confirmed that ultrafiltration effectively removes the biological interferences that make thiol oxidation necessary for untreated plasma. Icteric, uremic and slightly hemolyzed samples apparently do not affect the present assay, but grossly hemolyzed samples gave inaccurate results as judged by comparison with the reference method (data not shown). Other investigators have reported similar results for existing methods of carnitine assay. See. e.g., Secombe et al., Clin. Chem. 22, 589 (1976); Cederblad et al., Clin. Chem. 32, 342 (1986).

Linearity: The assay response was linear from 2 to 500 μmol/L. (Data not shown.)

Sensitivity. The lower detection limit for free L-carnitine by the present method was 2 μmol/L. (Data not shown.)

Precision. Intra-assay precision was determined by repeated analysis of the same pooled plasma ultrafiltrate using the present method. The values (mean±standard deviation) for free and total carnitine were 48.6 (±0.85) and 57.6 (±0.70) μmol/L, respectively (n=16). Inter-assay variation was calculated using different ultrafiltrates of the same pooled plasma over a period of about 3 weeks. Mean values were 50 (±2.0) and 57.6 (±1.3) μmol/L for free and total carnitine respectively (n=12). The inter-assay values obtained on the same specimens by the tandem mass spectrometric reference method were 46.6 (±1.89) and 53.5 (±2.18) μmol/L.

The foregoing examples are illustrative of the present invention, and are not to be construed as limiting thereof. The invention is defined by the following claims, with equivalents of the claims to be included therein.

That which is claimed is:

1. A method of quantifying free L-carnitine in a plurality of essentially protein-free biological fluid samples, comprising the steps of:
   (a) adding a plurality of essentially protein-free biological fluid samples to a plurality of wells in a centrifugal spectrophotometric analyzer rotor; then
   (b) adding to each of the plurality of samples:
      (i) acetyl coenzyme A (coA) in an amount sufficient to react with essentially all the free L-carnitine in the sample to produce acetylcarnitine and free coenzyme A; and
      (ii) 5,5'-dithiobis-2-nitrobenzoic acid in an amount sufficient to convert to thiophenylate essentially all free coenzyme A produced by the reaction of free L-carnitine and acetyl coenzyme A (coA); then
   (c) simultaneously centrifugally combining with each of the plurality of samples carnitine acetyltransferase in an amount sufficient to start reaction of the acetyl coenzyme A with the free L-carnitine to convert essentially all free L-carnitine in the sample to acetylcarnitine and free coenzyme A; then
   (d) simultaneously spectrophotometrically determining the amount of thiophenylate present in each of the plurality of samples.

2. A method according to claim 1, wherein said essentially protein-free biological fluid samples are selected from the group consisting of blood plasma and blood serum.

3. A method according to claim 2, wherein said essentially protein-free biological fluid samples are produced by ultrafiltrating biological fluid samples to remove essentially all proteins and protein-bound carnitine therefrom.

4. A method according to claim 3, wherein said ultrafiltration step is carried out using a filter with a molecular weight cutoff between 20,000 and 40,000 daltons.

5. A method according to claim 3, wherein said ultrafiltration step is carried out using an anisotropic hydrophilic membrane filter.

6. A method according to claim 1 wherein the spectrophotometric assessment measures the absorption of light with a wavelength between 400–420 nm.

7. A method of quantifying short-chain acylcarnitine in a plurality of essentially protein-free biological fluid samples, comprising the steps of:
(a) adding a plurality of essentially protein-free biological fluid samples to a plurality of wells in a centrifugal spectrophotometric analyzer rotor; then
(b) adding to each of the plurality of samples an alkaline solution capable of hydrolyzing essentially all short-chain acylcarnitine in the sample to free L-carnitine; then
(c) adding to each of the plurality of samples:
(i) acetyl coenzyme A (coA) in an amount sufficient to react with essentially all the free L-carnitine in the sample to produce acetylcarnitine and free coenzyme A; and
(ii) 5,5'-dithiobis-2-nitrobenzoic acid in an amount sufficient to convert to thiophenylate essentially all free coenzyme A produced by the reaction of free L-carnitine and acetyl coenzyme A (coA); then
(d) neutralizing the pH of each of the plurality of samples; then
(e) simultaneously centrifugally combining with each of the plurality of samples carnitine acetyltransferase in an amount sufficient to start reaction of the acetyl coenzyme A with the free L-carnitine to convert essentially all free L-carnitine in the sample to acetylcarnitine and free coenzyme A; then
(f) simultaneously spectrophotometrically determining the amount of thiophenylate present in each of the plurality of samples.

8. A method according to claim 7, wherein said essentially protein-free biological fluid samples are selected from the group consisting of blood plasma and blood serum.

9. A method according to claim 8, wherein said essentially protein-free biological fluid samples are produced by ultrafiltrating biological fluid samples to remove essentially all proteins and protein-bound carnitine therefrom.

10. A method according to claim 9, wherein said ultrafiltration step is carried out using a filter with a molecular weight cutoff between 20,000–40,000 daltons.

11. A method according to claim 9, wherein said ultrafiltration step is carried out using an anisotropic hydrophilic membrane filter.

12. A method of claim 7 wherein the spectrophotometric assessment measures the absorption of light with a wavelength between 400–420 nm.

13. A kit for carrying out the analysis of free L-carnitine and short-chain acylcarnitine in blood, comprising:
(a) a first container containing a solution comprising 5,5'-dithiobis-2-nitrobenzoic acid at a concentration of between 0.27 and 27 mmol/L and with a pH between 6.5–8.5; and
(b) a second container containing a solution comprising acetyl-coenzyme A (coA) at a concentration between 1.2 mmol/L and 120 mmol/L;
whereby the solutions of said first container and said second container can be mixed together prior to use to create a solution comprising 5,5'-dithiobis-2-nitrobenzoic acid at a concentration between 0.23 and 23 mmol/L and acetyl coenzyme A (coA) at a concentration between 0.17 to 17 mmol/L.

14. A kit according to claim 13, further comprising a third container containing carnitine acetyltransferase.

15. A kit according to claim 14, wherein said third container contains between 4 kU/L and 40 kU/L of carnitine acetyltransferase.

16. A kit according to claim 14, wherein said third container contains an aqueous solution comprising carnitine acetyltransferase with a concentration between 1.72 kU/L and 172 kU/L.

17. A kit according to claim 14, wherein said third container contains lyophilized carnitine acetyltransferase capable of being diluted with water to produce a solution with a concentration of carnitine acetyltransferase between 1.72 kU/L and 172 kU/L.

18. A kit according to claim 13, further comprising a container containing an aqueous solution comprising L-carnitine at a concentration between 0.1 and 10 mmol/L and octanoyl-L-carnitine at a concentration between 0.1 and 10 mmol/L.

19. A kit according to claim 13, further comprising a container containing a solution comprising 3-[N-morpholino]propanesulfonic acid in hydrochloric acid at a concentration of between 0.1 and 10 mol/L.

* * * * *

UNITED STATES PATENT AND TRADEMARK OFFICE
CERTIFICATE OF CORRECTION

PATENT NO. : 5,316,917

DATED : 31 May 1994

INVENTOR(S) : Diane S. Roe

It is certified that error appears in the above-identified patent and that said Letters Patent is hereby corrected as shown below:

Column 3, line 34, please correct " oxidizireagent " to read
   -- oxidizing reagent --.

Column 6, line 2, please correct " 96 " to read -- 86 --.

Column 10, line 13, please correct " 589 " to read
   -- 1589 --.

Signed and Sealed this

Sixth Day of September, 1994

*Attest:*

BRUCE LEHMAN

*Attesting Officer*   Commissioner of Patents and Trademarks